(12) United States Patent
Singhal et al.

(10) Patent No.: US 8,388,678 B2
(45) Date of Patent: Mar. 5, 2013

(54) MEDICAL DEVICES HAVING POROUS COMPONENT FOR CONTROLLED DIFFUSION

(75) Inventors: Anurag Singhal, Ashland, MA (US);
Robert A. Herrmann, Boston, MA (US); Yixin Xu, Newton, MA (US);
Young-Ho Song, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 439 days.

(21) Appl. No.: 12/333,909

(22) Filed: Dec. 12, 2008

(65) Prior Publication Data

US 2009/0157166 A1    Jun. 18, 2009

Related U.S. Application Data

(60) Provisional application No. 61/007,303, filed on Dec. 12, 2007.

(51) Int. Cl.
*A61F 2/06* (2006.01)
(52) U.S. Cl. ........................ 623/1.42; 623/1.46; 623/1.39
(58) Field of Classification Search .................. 623/1.42, 623/1.44, 1.39, 1.4
See application file for complete search history.

(56) References Cited

U.S. PATENT DOCUMENTS

| | | | | |
|---|---|---|---|---|
| 4,621,066 A * | 11/1986 | Nishigaki et al. | ............. | 501/128 |
| 4,789,649 A * | 12/1988 | Abert et al. | ........................ | 501/3 |
| 4,911,625 A * | 3/1990 | Begg et al. | ........................ | 419/6 |
| 5,733,925 A | 3/1998 | Kunz et al. | ..................... | 514/449 |
| 5,795,626 A | 8/1998 | Gabel et al. | | |
| 6,074,135 A | 6/2000 | Tapphorn et al. | | |
| 6,099,561 A * | 8/2000 | Alt | .............................. | 623/1.44 |
| 6,156,435 A | 12/2000 | Gleason et al. | ................ | 428/422 |
| 6,517,888 B1 | 2/2003 | Weber | ........................... | 427/2.24 |
| 2002/0142579 A1 | 10/2002 | Vincent et al. | ................ | 438/623 |
| 2002/0168466 A1 | 11/2002 | Tapphorn et al. | | |
| 2003/0006250 A1 | 1/2003 | Tapphorn et al. | | |

(Continued)

FOREIGN PATENT DOCUMENTS

| | | |
|---|---|---|
| WO | 98/52494 A1 | 11/1998 |
| WO | 02/085532 A1 | 10/2002 |

(Continued)

OTHER PUBLICATIONS

Tejal A. Desai et al., "Characterizatoin of Micromachined Silicon Membranes for Immunoisolation and bioseparation Applications", *J. Membrane Science*, 159, 1999, pp. 221-231.

(Continued)

*Primary Examiner* — Thomas J Sweet
*Assistant Examiner* — Seema Mathew
(74) *Attorney, Agent, or Firm* — Mayer & Williams PC; David B. Bonham; Keum J. Park (57) ABSTRACT

According to an aspect of the present invention, implantable or insertable medical devices are provided which contain the following: (a) substrate having one or more depressions that contain at least one therapeutic agent and (b) a porous membrane disposed over the substrate and the one or more depressions, which regulate transport of chemical species between the therapeutic-agent-containing depressions and the exterior of the device. The substrate and the porous membrane are formed of different materials each with a different thermal expansion coefficient. Moreover, one of the substrate and the porous membrane at least partially surrounds the other. Other aspects of the present invention are directed to methods of making such medical devices, and methods of treatment using such medical devices.

20 Claims, 5 Drawing Sheets

U.S. PATENT DOCUMENTS

| | | | |
|---|---|---|---|
| 2003/0028243 A1 | 2/2003 | Bates et al. | |
| 2003/0064095 A1 | 4/2003 | Martin et al. | 424/451 |
| 2003/0083646 A1* | 5/2003 | Sirhan et al. | 604/891.1 |
| 2003/0138645 A1 | 7/2003 | Gleason et al. | 428/447 |
| 2004/0148015 A1 | 7/2004 | Lye et al. | 623/1.15 |
| 2004/0204750 A1 | 10/2004 | Dinh et al. | 623/1.15 |
| 2005/0060020 A1* | 3/2005 | Jenson | 623/1.13 |
| 2005/0070989 A1 | 3/2005 | Lye et al. | 623/1.4 |
| 2005/0119723 A1* | 6/2005 | Peacock, III | 623/1.15 |
| 2005/0208100 A1* | 9/2005 | Weber et al. | 424/426 |
| 2006/0127443 A1 | 6/2006 | Helmus et al. | 424/423 |
| 2006/0129215 A1 | 6/2006 | Helmus et al. | 607/115 |
| 2006/0276877 A1* | 12/2006 | Owens et al. | 623/1.15 |
| 2007/0073383 A1* | 3/2007 | Yip et al. | 623/1.16 |
| 2007/0135908 A1 | 6/2007 | Zhao | 623/1.46 |
| 2007/0191931 A1 | 8/2007 | Weber et al. | 623/1.38 |
| 2007/0191943 A1 | 8/2007 | Shrivastava et al. | 623/1.46 |
| 2007/0224116 A1 | 9/2007 | Chandrasekaran et al. | |
| 2007/0224235 A1* | 9/2007 | Tenney et al. | 424/423 |
| 2007/0224244 A1 | 9/2007 | Weber et al. | 424/426 |
| 2008/0051881 A1 | 2/2008 | Feng et al. | 623/1.39 |
| 2008/0109072 A1* | 5/2008 | Girton | 623/1.49 |
| 2008/0306584 A1* | 12/2008 | Kramer-Brown | 623/1.39 |
| 2009/0030504 A1* | 1/2009 | Weber et al. | 623/1.42 |
| 2009/0118821 A1* | 5/2009 | Scheuermann et al. | 623/1.49 |

FOREIGN PATENT DOCUMENTS

| | | |
|---|---|---|
| WO | 03086238 A1 | 10/2003 |

OTHER PUBLICATIONS

Heinrich Wieneke et al., "Synergistic Effects of a Novel Nanoporous Stent Coating and Tacrolimus on Intima Proliferation in Rabbits", *Catheterization and Cardiovascular Interventions*, 2003, vol. 60, 3, pp. 399-407.

Erin E. Leary Swan et al., "Fabrication and evaluation of nanoporous alumina membranes for osteoblast culture", *Journal of Biomedical Materials Research Part A*, vol. 72A, Issue 3, pp. 288-295, Published Online: Jan. 14, 2005.

Rita D'Aquino, "Good Drug Therapy: It's Not Just the Molecule—It's the Delivery", www.cepmagazine.org., Feb. 2004.

Thomas Lippert et al., "Chemical and Spectroscopix Aspects of Polymer Ablation: Special Features and Novel Directions", *Chem. Rev.*, 103, 2, pp. 453-485, Feb. 2003.

J. Meijer J. et al., "Laser Machining by short and ultrashort pulses, state of the art and new opportunities in the age of photons", *Annals of the CIRP*, 51, 2, pp. 531-550, 2002.

Lara Leoni et al., "Nanoporous Platforms for Cellular Sensing and Delivery", *Sensors*, 2, 2002, pp. 111-120.

Jonah Erlebacher et al., "Evolution of nanoporosity in de-alloying", *Nature*, vol., 410, 22 Mar. 2001, pp. 450-453.

A.J. Forty, "Corrosion micromorphology of noble metal alloys and depletion gilding", *Nature*, vol. 282, Dec. 6, 1979, pp. 597-598.

R.C. Newman et al., "Alloy Corrosion", *MRS Bulletin*, Jul. 1999, pp. 24-28.

Huixin He et al., "Electrochemical fabrication of metal nanowires" in *Encyclopedia of Nanoscience and Nanotechnology*, N.S. Nalwa, ed., American Scientific Publishers, 2003, vol. X, pp. 1-18.

Jong-Ah Paik et al., "Micromachining of mesoporous oxide films for microelectromechanical system structures", *J. Mater. Res.*, vol. 17, No. 8, Aug. 2002, p. 2121-2129.

K.K. S. Lau et al., "Hot-wire chemical vapor deposition (HWCVD) of fluorocarbon and organosilicon thin films", *Thin Solid Films*, 395, 2001, pp. 288-291.

Viitala R. et al., "Surface properties of in vitro bioactive and non-bioactive sol-gel derived materials," *Biomaterials*, 23, Aug. 23, 2002 15, pp. 3073-3086.

Tejal Desai et al., "Use of Microfabricated 'Nanopore' Membranes as a Rate-Limiting Barrier to Diffusion of Small and Large Molecules: Possible Role in Drug Delivery", http://www.healthtech.com/2001/mfb/abstracts/desai.htm. Jun. 12, 2003 download.

*Standard handbook of biomedical engineering and design*, Myer Kutz, ed., 2003, ISBN 0-07-135637-1, pp. 16.13-16.29.

Jung Yul Lim et al., "Systemic variation in osteoblast adhesion and phenotype with substratum surface characteristics", *J. Biomed. Mater. Res.*, 68A, 3, 2004, pp. 504-512.

R.G. Flemming et al., "Effects of synthetic micro- and nano-structured surfaces on cell behavior", *Biomaterials* 20, 1999, pp. 573-588.

Sarah Brody et al., "Characterizing Nanoscale Topography of the Aortic Heart Valve Basement Membrane for Tissue Engineering Heart Valve Scaffold Design", *Tissue Eng.*, Feb. 12, 2006 2, pp. 413-421.

Steven L. Goodman et al., "Three-dimensional extracellular matrix textured biomaterials", *Biomaterials* , 1996, 17, pp. 2087-2095.

Jeffrey M. Caves et al., "The evolving impact of microfabrication and nanotechnology on stent design", *J. Vasc. Surg.*, 44, 2006, pp. 1363-1368.

*ASM Ready Reference: Thermal properties of Metals*, ASM International, Materials Park, Ohio, USA, 2002, pp. 9-16.

W.D. Callister, *Materials Science and Engineering: An Introduction*, 7th Edition, 2006, p. W5.

Mark A. Occhionero et al., "Aluminum Silicon Carbide (AlSiC) Microprocessor Lids and Heat Sinks for Integrated Thermal Management Solutions", 2000 HDI Conf., Denver, CO, Apr. 26-28, 2000, pp. 1-5.

"Chart of COE's Coefficient of Thermal Expansion" downloaded Mar. 2, 2007 from http://www.lucasmilhaupt.com.

D. Shamiryan et al., "Comparative study of SiOCH low-k films with varied porosity interacting with etching and cleaning plasma," *J. Vac. Sci. Technol. B*, 20(5), Sep./Oct. 2002, pp. 1923-1928.

Shula Radin et al., "In vitro bioactivity and degradation behavior of silica xerogels intended as controlled release materials," *Biomaterials* , Aug. 23, 15, 2002, pp. 3113-3122.

Steven B. Nicoll et al., "In vitro release kinetics of biologically active transforming growth factor-beta 1 from a novel porous glass carrier," *Biomaterials.*, Jun. 18, 1997, 12, pp. 853-859.

Erick M. Santos et al., "Sol-gel derived carrier for the controlled release of proteins," *Biomaterials*. Sep. 20, 1999, 18, pp. 1695-1700.

S. Radin et al., "Silica sol-gel for the controlled release of antibiotics. I. Synthesis, characterization, and in vitro release," *J Biomed Mater Res.*, Nov, 57, 2, 2001, pp. 313-320.

W. Aughenbaugh et al., "Silica sol-gel for the controlled release of antibiotics. II. The effect of synthesis parameters on the in vitro release kinetics of vancomycin," *J Biomed Mater Res* , Dec. 5, 57 3, 2001, pp. 321-326.

Erick M. Santos et al., "Si—Ca—P xerogels and bone morphogenetic protein act synergistically on rat stromal marrow cell differentiation in vitro," *J Biomed Mater Res.*, July 41,1, 1998, pp. 87-94.

H. Biederman et al., "Plasma Polymer-Metal Composite Films", in Plasma Deposition, Treatment, and Etching of Polymers, Riccardo d'Agostino, Ed., Academic Press (1990) pp. 269-320.

Y. Gao, "Chemical Vapor Deposition", Chap. 5 in Handbook of Nanophase and Nanostructured Materials, vol. 1: Synthesis, Zhong Lin Wang, Yi Liu, and Ze Zheng, Eds., Kluwer Academic/Plenum Publishers (2002), pp. 102-139.

\* cited by examiner

MEDICAL DEVICES HAVING POROUS COMPONENT FOR CONTROLLED DIFFUSION

STATEMENT OF RELATED APPLICATIONS

This application claims the benefit of U.S. Provisional Patent Application Ser. No. 61/007,303, filed Dec. 12, 2007, entitled "Medical Devices Having Porous Component For Controlled Diffusion", which is incorporated in its entirety by reference herein.

TECHNICAL FIELD

This invention relates to medical devices, and more particularly, to medical devices that utilize porous materials for diffusion control.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time, in order to deliver therapeutic agents to the target site.

H. Wieneke, et al., "Synergistic effects of a novel nanoporous stent coating and tacrolimus on intima proliferation in rabbits," *Catheterization and Cardiovascular Interventions*, Volume 60, Issue 3, pp. 399-407, describe stainless steel coronary stents that are provided with a ceramic nanoporous aluminum oxide ($Al_2O_3$) coating, which is used as a carrier for tacrolimus. Similarly, Pub. No. US 2005/0070989, describes implantable medical devices such as stents, which have nanoporous layers that are loaded with therapeutic agents. Pub. No. US 2006/0127443 to Helmus et al. is directed to medical devices which contain a vapor deposited nanoporous coating (e.g., a polymeric, ceramic or metallic nanoporous coating) disposed over a therapeutic-agent containing region, which regulates the release of the therapeutic agent from the medical device when it is placed into a subject.

SUMMARY OF THE INVENTION

According to an aspect of the present invention, implantable or insertable medical devices are provided which contain the following: (a) substrate having one or more depressions that contain at least one therapeutic agent, and (b) a porous membrane disposed over the one or more depressions, which regulate transport of chemical species between the therapeutic-agent-containing depressions and the exterior of the device. The substrate and the porous membrane are formed of different materials each with a different thermal expansion coefficient. Moreover, one of the substrate and the porous membrane at least partially surrounds the other.

Other aspects of the present invention are directed to methods of making such medical devices, and methods of treatment using such medical devices.

An advantage of the present invention is that tubular medical devices may be provided, in which the transport of chemical species into the medical device, out of the medical device, or both are controlled.

Another advantage of the present invention is that tubular medical devices may be provided, which contain porous materials for diffusion control and which contain quantities of therapeutic agents exceeding the void volume within the porous material.

Yet another advantage of the present invention is that tubular medical devices may be provided, which contain porous materials for diffusion control, and for which it is not necessary to pass therapeutic agent through the porous materials when loading the medical devices with the therapeutic agent.

These and other embodiments and advantages of the present invention will become readily apparent to those of ordinary skill in the art upon review of the Detailed Description and Claims to follow.

DETAILED DESCRIPTION

According to an aspect of the present invention, implantable or insertable medical devices are provided which contain the following: (a) substrate having one or more depressions that contain at least one therapeutic agent and (b) a porous membrane disposed over the one or more depressions, which regulate transport of chemical species (e.g., in many embodiments, the therapeutic agent, among others) between the therapeutic-agent-containing depressions and the exterior of the device. The substrate and the porous membrane are formed of different materials each with a different thermal expansion coefficient (TEC). Moreover, one of the substrate and the porous membrane at least partially surrounds (e.g., encircles) the other of the substrate and the porous membrane.

In preferred embodiments, one component (i.e., the substrate or the porous membrane) has a TEC that is at least 10% higher than the other component at room temperature, for example, ranging from 10% higher to 20% higher to 50% higher to 100% higher, or more.

As used herein a "membrane" is a thin article of material (e.g., in the form of a sheet, annulus, hollow hemisphere, etc.) that is permeable to certain chemical substances.

The substrate, the porous membrane, or both, may be selected from a variety of materials including (a) organic materials (e.g., materials containing 50 wt % or more organic species) such as polymeric materials, and (b) inorganic materials (e.g., materials containing 50 wt % or more inorganic species), such as metallic materials (e.g., metals and metal alloys) and non-metallic inorganic materials (e.g., including carbon, semiconductors, glasses and ceramics).

As noted above, in the devices of the present invention, the substrate and the porous membrane are formed of different materials each with a different TEC, and one of the substrate and the porous membrane partially or fully surrounds the other.

In some embodiments, the substrate has a higher TEC than the porous membrane. In other embodiments, the porous membrane has a higher TEC than the substrate. Depending upon which component at least partially surrounds the other, the components will reduce their engagement with one another upon heating or upon cooling. For example, if the component with the higher TEC surrounds the component with the lower TEC, upon heating the higher TEC component will expand more than the lower TEC component and loosen its engagement with the same. Conversely, if the component with the lower TEC surrounds the component with the higher TEC, upon cooling, the higher TEC component will shrink more than the lower TEC component and reduce its engagement with the same.

As indicated above, the porous membrane regulates transport of chemical species between one or more therapeutic-agent-containing depressions in the device substrate and the exterior of the device. The therapeutic agent may be, for example, disposed for release within the medical device, in which case the porous membrane may regulate transport of the therapeutic agent from the depression(s) within which it is disposed to the exterior of the device such that it is released in vivo. The therapeutic agent may be, for example, immobilized within the medical device, in which case the porous membrane may regulate transport of an in vivo chemical species from the bodily environment surrounding the device into the depressions (where they may, for example, chemically react with the therapeutic agent, bind with the therapeutic agent, etc.). Where chemical species from the bodily environment surrounding the device chemically react with the therapeutic agent in the depression(s), the porous membrane may regulate transport of chemical products of the reaction (which may be, for example, less detrimental or more beneficial that the reacted species) from the depression(s) to the exterior of the device.

Implantable or insertable medical devices which can be constructed in accordance with the invention vary widely and include, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, catheters (e.g., urological catheters or vascular catheters such as balloon catheters and various central venous catheters), guide wires, filters (e.g., vena cava filters and mesh filters for distil protection devices), embolization devices including cerebral aneurysm filler coils (including Guglielmi detachable coils and metal coils), septal defect closure devices, drug depots that are adapted for placement in an artery for treatment of the portion of the artery distal to the device, myocardial plugs, pacemakers, leads including pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, fins and fusion devices, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other devices that are implanted or inserted into the body.

The medical devices of the present invention include, for example, implantable and insertable medical devices that are used for systemic diagnosis or treatment, as well as those that are used for the localized diagnosis or treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

Medical devices benefiting from the present invention thus include a variety of implantable and insertable medical devices including devices for insertion into and/or through a wide range of body lumens, for purposes of diagnosis or treatment, several of which are recited above, including lumens of the cardiovascular system such as the heart, arteries (e.g., coronary, femoral, aorta, iliac, carotid and vertebrobasilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract such as the trachea, bronchi, nasal passages and sinuses, lumens of the gastrointestinal tract such as the esophagus, gut, duodenum, small intestine, large intestine, rectum, biliary and pancreatic duct systems, lumens of the lymphatic system, the major body cavities (peritoneal, pleural, pericardial) and so forth.

As used herein, terms such as "treatment" and "therapy" refers to the prevention of a disease or condition, the reduction or elimination of symptoms associated with a disease or condition, or the substantial or complete elimination of a disease or condition.

Preferred subjects for treatment or diagnosis are vertebrate subjects, for example, humans, livestock and pets.

In some embodiments, the substrate and the porous membrane are both tubular (e.g., stents, tubing, etc.). In such embodiments, the one or more depressions may be provided within the abluminal surface of the tubular substrate, and the porous tubular membrane may be disposed over the abluminal surface. Alternatively, the one or more depressions may be provided within the luminal surface of the tubular substrate, and the porous tubular membrane may be disposed over the luminal surface of the substrate. As another alternative, among others, the one or more depressions may be provided within each of the luminal and abluminal surfaces of the tubular substrate, and porous tubular membranes (one with a TEC higher than that of the substrate and the other having a TEC lower than that of the substrate) may be disposed over the luminal and abluminal surface of the substrate.

Figure 1A:
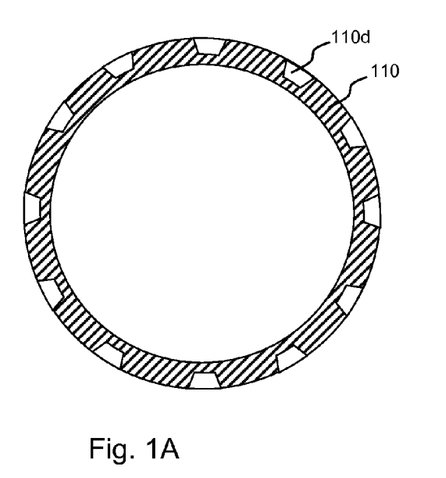
FIGS. 1A-1D are schematic cross-sectional views illustrating a method of forming a tubular medical device, in accordance with an embodiment of the invention.
Figure 1B:
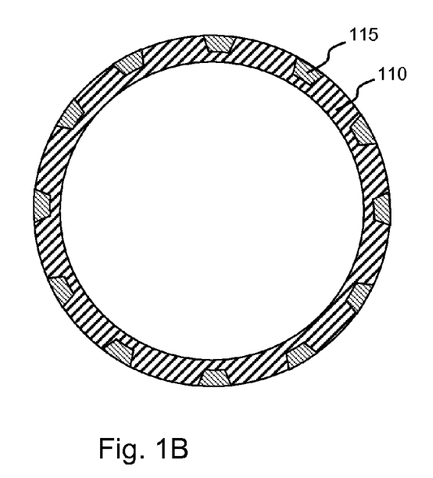

By way of example, FIG. 1A is a schematic cross-section illustrating a tubular medical device substrate 110, which contains depressions 110d on its outer (abluminal) surface, which can be filled with a therapeutic-agent-containing composition 115 as shown in FIG. 1B. The therapeutic-agentcontaining composition 115 may consist essentially of one or more therapeutic agents, or it may contain further optional agents such as polymer matrix materials, diluents, excipients or fillers. Moreover, all of the depressions 110d may be filled with the same therapeutic-agent-containing composition 115, or some depressions may be filled with a first therapeutic-agent-containing composition while other depressions may be filled with a different therapeutic-agent-containing composition, among other possibilities.

Figure 1C:
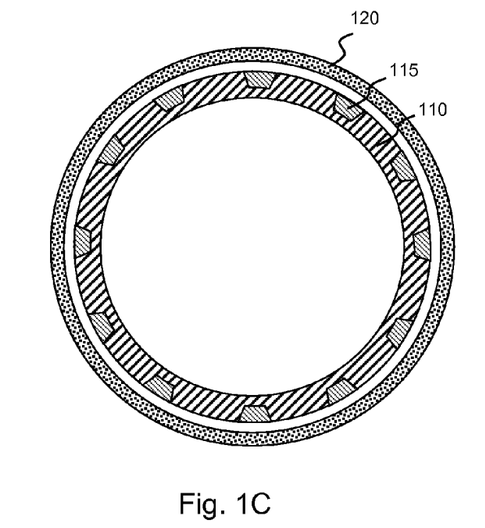
Figure 1D:
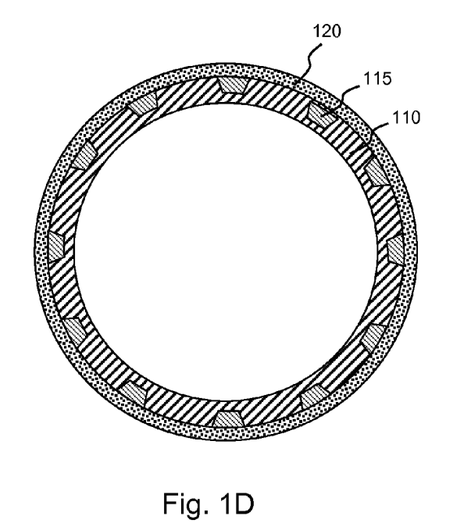

As shown in FIG. 1C, the substrate 110 and porous membrane 120 are sized such that the substrate 110 can be inserted into a porous membrane 120 at either elevated or depressed temperatures. Upon returning to ambient temperature (i.e., in the range of from 10 to 40° C.), the substrate 110 and porous membrane 120 engage one another as shown in FIG. 1D. For example, if the substrate 110 has a higher TEC than the porous membrane 120 (e.g., a relatively high TEC metallic or polymeric substrate coupled with a relatively low TEC metallic or non-metallic inorganic porous membrane, among other possibilities), the substrate 110 may be inserted into the porous membrane 120 at a depressed temperature. Upon warming, the substrate 110 expands more than the porous membrane 120, allowing the two components to engage one another as shown in FIG. 1D. Conversely, if the substrate 110 has a lower TEC than the porous membrane 120 (e.g., a relatively low TEC metallic or non-metallic inorganic substrate coupled with a relatively high TEC metallic or polymeric porous membrane, among other possibilities), the substrate 110 may be inserted into the porous membrane 120 at an elevated temperature. Upon cooling, the porous membrane 120 will contract more than the substrate 110, allowing the two components to engage one another as shown in FIG. 1D. In these embodiments, the substrate 110 should be of sufficient rigidity such that it is able to effectively engage the porous membrane 120 upon a return to ambient temperature (e.g., without deforming, buckling, etc.).

Figure 3A:
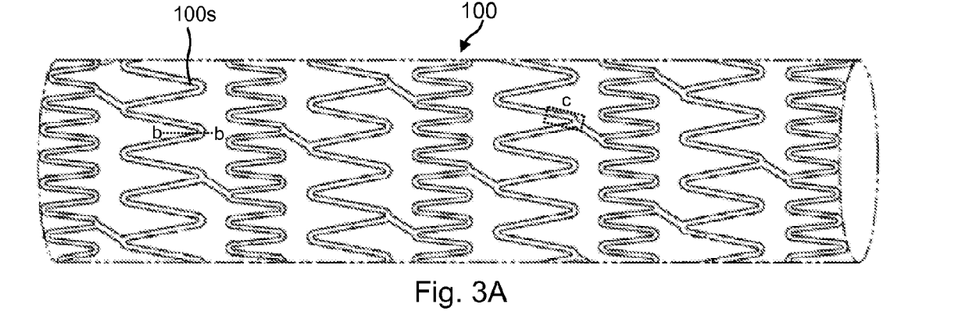
FIG. 3A is a schematic perspective view of a stent in accordance with an embodiment of the invention.
Figure 3B:
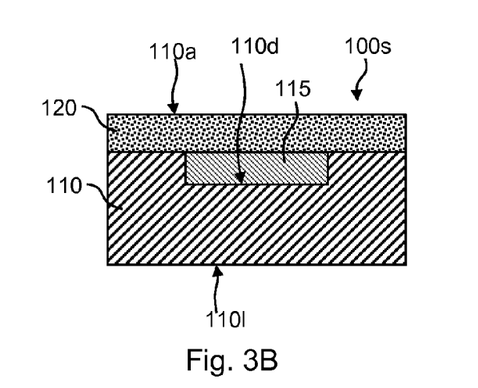
FIG. 3B is a schematic cross-sectional view taken along line b-b of FIG. 3A.
Figure 3C:
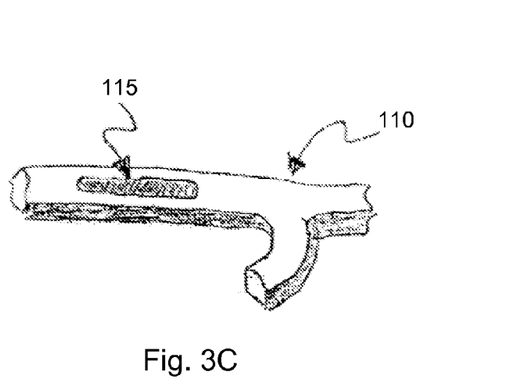
FIG. 3C is a schematic perspective view of a portion of the stent of FIG. 3A, with the porous membrane removed.

A procedure of this type may be used to form a medical device like that shown in FIG. 3A, which is a schematic perspective view of a stent 100 which contains a number of interconnected struts 100s. FIG. 3B is a cross-section taken along line b-b of strut 100s of stent 100 of FIG. 3A, which has an abluminal surface 100a and a luminal surface 100l. The following are shown in FIG. 3B: a strut substrate 110, a depression 110d, which is filled with a therapeutic-agent-containing composition 115, and a porous membrane 120, which is disposed over the strut substrate 110 and the depression 110d filled with the therapeutic-agent-containing composition 115. FIG. 3C is a perspective view of a portion of the stent 100 in FIG. 3A (designated by reference letter c), with the porous membrane removed to shown the shape of the depression in the substrate 110 that is filled with the therapeutic-agent-containing composition 115. For example, such a structure may be formed by first creating a structure like that described above in conjunction with FIG. 1D, in which a drug-loaded tubular substrate is inserted into a tubular porous membrane at depressed/elevated temperature and the resulting assembly is heated/cooled to ambient temperature to tightly engage the tubular substrate and tubular porous membrane. This is then followed by a process in which the tubular structure is cut (e.g., by laser or mechanical cutting) to create a stent 100 with struts 100s like that shown in FIGS. 3A-3C.

Figure 11:
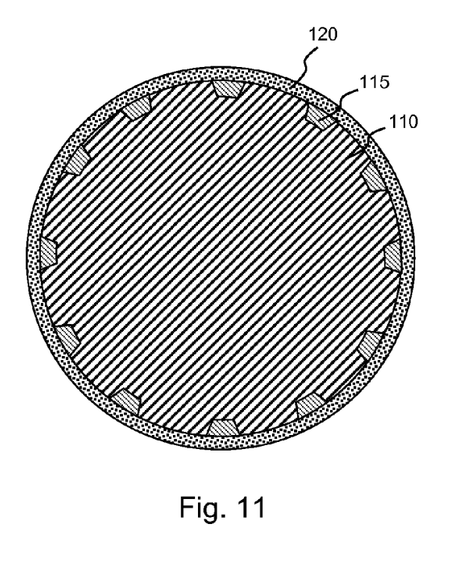

A schematic cross-sectional illustration of a device in accordance with another embodiment of the invention is shown in FIG. 11. This device is similar to that of FIG. 1D, except that the substrate 110 is of circular (solid) cross-section rather than annular (hollow) cross-section. Examples of devices of this type include, for example, embolic spheres, embolic rods, and orthopedic implants, among many others.

Figure 9:
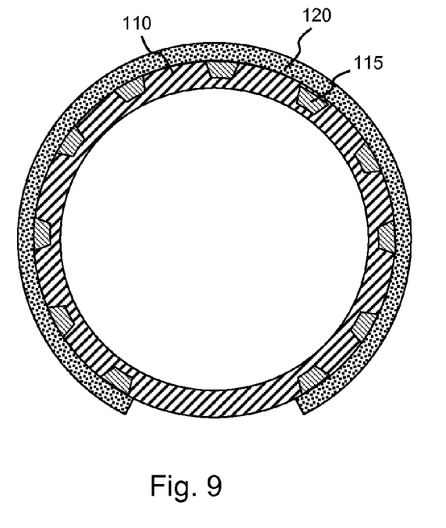
FIGS. 9-11 are schematic cross-sectional view illustrating medical devices in accordance with further embodiments of the invention.

As noted above, the porous region may partially or fully surround (e.g., encircle) the substrate, or vice versa. For example, FIG. 9 is similar to FIG. 1D in that it is a schematic cross-section illustrating a substrate 110 with depressions containing a therapeutic-agent-containing composition 115 and a porous membrane 120 disposed over the same. However, in FIG. 1D, the porous membrane 120 entirely encircles the substrate 110, whereas in FIG. 9 the porous membrane 120 only partially encircles the substrate 110. In these embodiments, the porous membrane 120 and the substrate 110 should both be of sufficient rigidity such that they are able to effectively engage one another upon heating/cooling to ambient temperature.

Figure 2A:
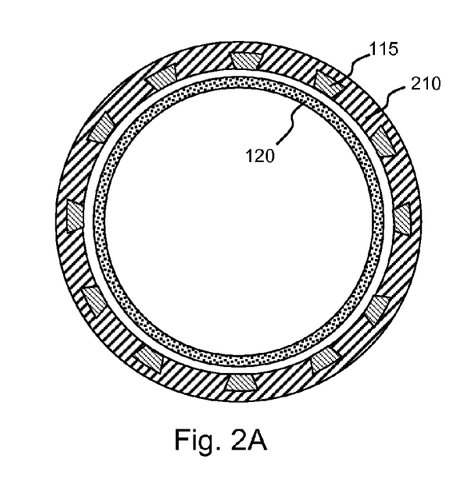
FIGS. 2A-2B are schematic cross-sectional views illustrating a method of forming a tubular medical device, in accordance with another embodiment of the invention.
Figure 2B:
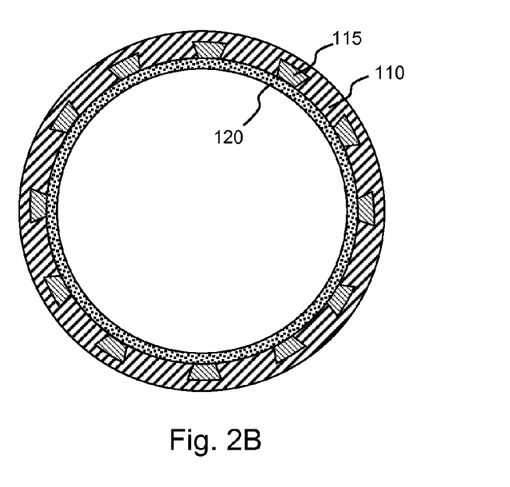

Turning now to FIG. 2A, there is shown a schematic cross-section illustrating a tubular porous membrane 120 inserted into a tubular medical device substrate 110, which contains depressions on its luminal surface that are filled with a therapeutic-agent-containing composition 115. Analogous to the device of FIG. 1C, the porous membrane 120 can be inserted into the substrate 110 at either elevated or depressed temperatures. Upon returning to ambient temperature, the substrate 110 and porous membrane engage one another as shown in FIG. 2B. For example, if the substrate 110 has a lower TEC than the porous membrane 120, the porous membrane 120 is inserted into the substrate 110 at a depressed temperature. Upon warming, the porous membrane 120 will expand more than the substrate 110, allowing the two components to tightly engage one another as shown in FIG. 2B. Conversely, if the substrate 110 has a higher TEC than the porous membrane 120, the porous membrane 120 is inserted into the substrate 110 at elevated temperature. Upon cooling, the substrate 110 will contract more than the porous membrane 120, allowing the two components to engage one another as shown in FIG. 2B. In these embodiments, the porous membrane 120 should be of sufficient rigidity such that it is able to effectively engage the substrate 110 upon heating/cooling.

Figure 10:
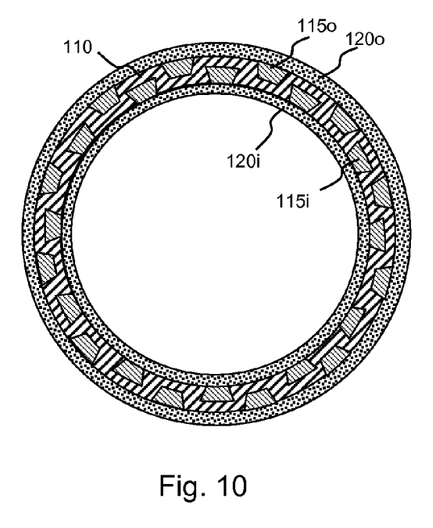

In other embodiments, multiple porous membranes may be employed. For example, turning to FIG. 10, there is shown a schematic cross-section illustrating a tubular medical device substrate 110, which contains depressions on its luminal surface that are filled with a therapeutic-agent-containing composition 115i and depressions on its abluminal surface that are filled with a therapeutic-agent-containing composition 115o. An outer tubular porous membrane 120o encircles the tubular substrate 110, which in turn encircles an inner tubular porous membrane 120i. Analogous to the above devices, an assembly may be formed at elevated or depressed temperatures in which the inner tubular porous membrane 120i is disposed within the tubular substrate 110, which in turn is disposed within the outer tubular porous membrane 120o. Upon returning to ambient temperature, the substrate 110 and porous membranes 120i, 120o tightly engage one another as shown in FIG. 10. For example, if inner porous membrane 120i has a TEC that is higher than the substrate 110, which in turn has a TEC that is higher than the outer porous membrane 120o, the assembly is formed at lower temperatures. Upon warming, the inner porous membrane 120i will expand more than the substrate 110, which will in turn expand more than the outer porous membrane 120o, causing the components 110, 120i, 120o to more tightly engage one another. Conversely, if the inner porous membrane 120i has a TEC that is lower than the substrate 110, which in turn has a TEC that is lower than the outer porous membrane 120o, the assembly is formed at higher temperatures. Upon cooling, the outer porous membrane 120o will shrink more than the substrate 110, which will in turn shrink more than the inner porous membrane 120*i*, causing the components 110, 120*i*, 120*o* to engage one another. In these embodiments, the porous membrane 120*i* and the substrate 110 should be of sufficient rigidity such that they are able to effectively engage outlying components without excessive deformation upon heating/cooling.

As indicated above, it is possible to provide different therapeutic agents at different locations on the medical device. In an embodiment like that of FIG. 10, for example, it is possible to provide one or more first depressions that are filled with a first therapeutic agent 115*i* (e.g., an anti-inflammatory agent, an endothelialization promoter or an antithrombotic agent) at the inner, luminal surface of the substrate 110, and one or more second depressions filled with a second therapeutic agent 115*o* that differs from the first therapeutic agent (e.g., an anti-restenotic agent) at the outer, abluminal surface if the substrate 110.

Of course, there are configurations other than tubular or partial tubular configurations in which a porous membrane encircles a substrate, or vice versa, and thus can more tightly engage one another based on differences in TEC and temperature changes as discussed above. For example, turning now to FIG. 7A, there is shown a schematic perspective view illustrating a disk shaped porous membrane 120 and a medical device substrate 110 having a depression (i.e., a reservoir) that is at least partially filled with a therapeutic-agent-containing composition 115. The porous membrane 120 may be inserted into a recess 110*r* in the medical device substrate 110, such that it is disposed over the therapeutic-agent-containing composition 115. Analogous to the above, the porous membrane 120 can be inserted into the recess 110*r* of the substrate 110 at either elevated or depressed temperatures. Upon returning to ambient temperature, the substrate 110 and porous membrane 120 engage one another as shown in FIG. 7B. For example, if the substrate 110 has a lower TEC than the porous membrane 120, the porous membrane 120 is inserted into the substrate 110 at low temperature. Upon warming, the porous membrane 120 will expand more than the substrate 110, allowing the two components to engage one another as shown in FIG. 7B. Conversely, if the substrate 110 has a higher TEC than the porous membrane 120, the porous membrane 120 is inserted into the substrate 110 at elevated temperature. Upon cooling, the substrate will contract more than the porous membrane 120, allowing the two components to engage one another as shown in FIG. 7B. In either case, the porous membrane 120 should be of sufficient rigidity such that it is able to effectively engage the substrate 110 upon heating/cooling (e.g., without buckling or other excessive deformation).

Nor are the geometries of the medical devices of the invention restricted to circular geometries. For example, turning now to FIG. 8, there is shown a schematic perspective view illustrating a rectangular porous membrane 120 inserted into a recess in a medical device substrate 110. As with FIG. 7A, the medical device substrate 110 has a depression (i.e., a reservoir, not shown) that is at least partially filled with a therapeutic-agent-containing composition (not shown). Analogous to the above, the porous membrane 120 can be inserted into a recess of substrate 110 at either elevated or depressed temperatures (depending upon the respective TECs of the materials). Upon returning to ambient temperature, the substrate 110 and porous membrane 120 tightly engage one another.

Figure 7A:
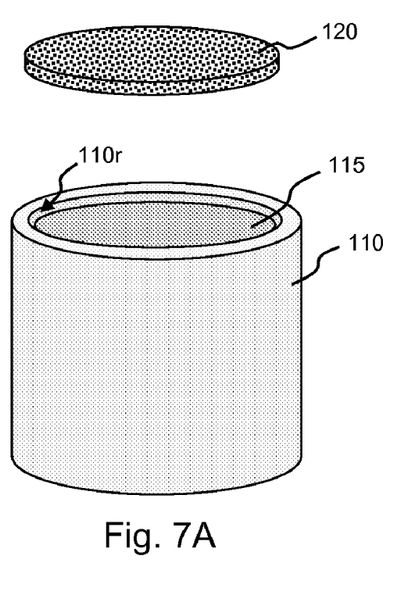
FIGS. 7A-7B are schematic perspective views illustrating a method of forming a medical device, in accordance with an embodiment of the invention.
Figure 7B:
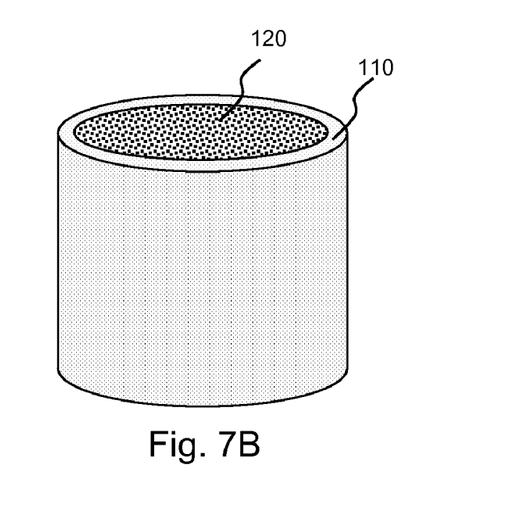
Figure 8:
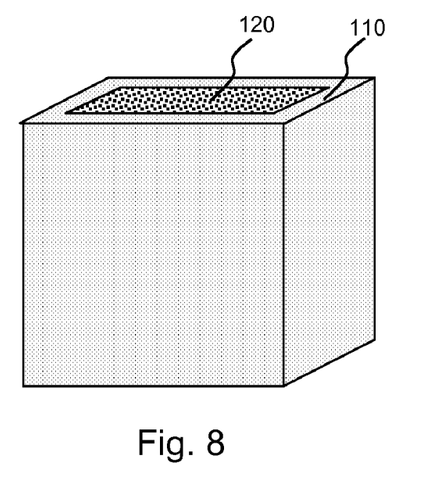
FIG. 8 is a schematic perspective view of a medical device, in accordance with an embodiment of the invention.

In one specific embodiment, a stent may be provided with numerous cavities of suitable size and shape (e.g. a cavity with a circular mouth like that of FIGS. 7A and 7B or a square mouth like that of FIG. 8, among numerous other possible shapes). For example, the cavities may be provided on the luminal stent surface, the abluminal stent surface, the side stent surfaces (e.g., the cavities may be provided on the ends of the stent for selective end release, for instance, for edge protection), or a combination of the foregoing. After inserting a therapeutic-agent-containing material into the cavities, a porous membrane (e.g. a circular membrane like that of FIGS. 7A and 7B or a square membrane like that of FIG. 8, among numerous other possible shapes) is inserted into each of the cavities at either elevated or depressed temperatures, depending upon the respective TECs of the materials. For example, the membrane may be inserted such that it rests upon a lip that is provided at the entrance to each cavity. Upon returning to ambient temperature, the stent substrate and porous membranes tightly engage one another.

As seen from the above, the substrate may have single or multiple (e.g., 1 to 2 to 5 to 10 to 25 to 50 to 100 or more) therapeutic-agent-containing depressions. Therapeutic-agent-containing depression(s) may be provided over the entire device or only over one or more distinct portions of the device. For example, as seen from the above, for tubular devices such as stents, therapeutic-agent-filled depression(s) with associated porous membrane(s) may be provided on the luminal device surfaces, on the abluminal device surfaces, on the side surface, or a combination of two or more of the luminal, abluminal and side surfaces.

Figure 4A:
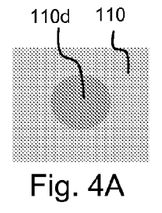
FIGS. 4A-4G and 5A-5E are schematic top views illustrating various depression configurations and arrays of the same, which may be employed in various embodiments of the invention.
Figure 4B:
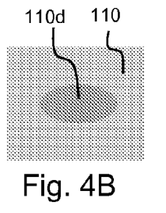
Figure 4C:
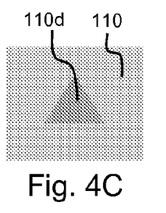
Figure 4D:
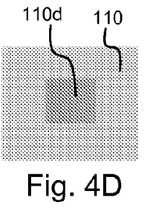
Figure 4E:
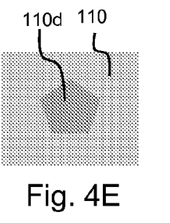
Figure 4F:
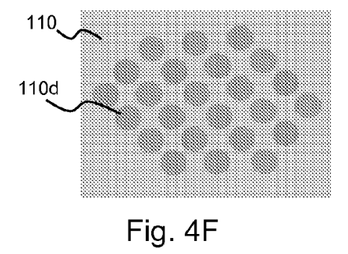
Figure 4G:
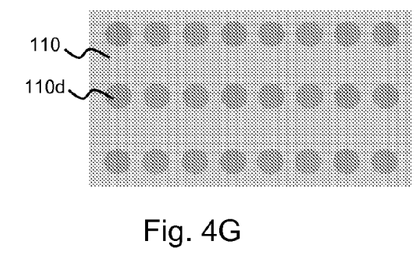
Figure 5A:
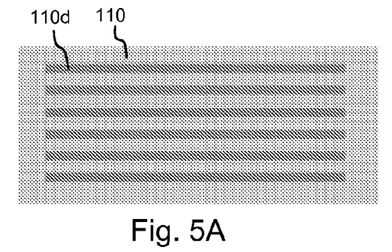
Figure 5B:
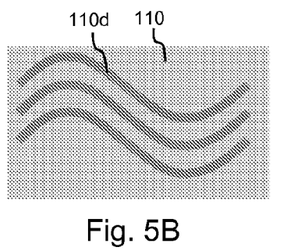
Figure 5C:
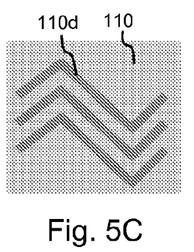
Figure 5D:
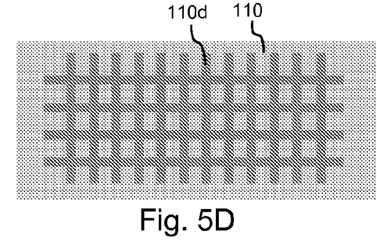
Figure 5E:
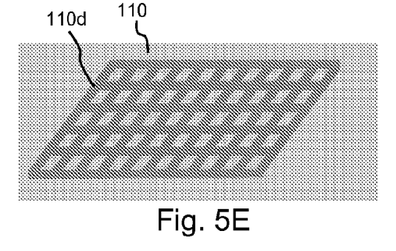

The depressions which contain the therapeutic agents may come in various shapes and sizes and can extend partially or completely through the substrate. (As a specific example of the latter case, a structure like that of FIG. 10 can be provided with depressions that extend through the substrate.) Examples include depressions whose lateral dimensions are circular (see, e.g., the top view of the circular hole of FIG. 4A, in which the depressed area 110*d* within the medical device substrate 110 is designated with a darker shade of grey), oval (see FIG. 4B), polygonal, for instance triangular (see FIG. 4C), quadrilateral (see FIG. 4D), penta-lateral (see FIG. 4E), as well as depressions of various other regular and irregular shapes and sizes. Multiple depressions 110*d* can be provided in a near infinite variety of arrays. See, e.g., the depressions 110*d* shown in FIGS. 4F and 4G. Further examples of depressions 110*d* include trenches, such as simple linear trenches (see FIG. 5A), wavy trenches (see FIG. 5B), trenches formed from linear segments whose direction undergoes an angular change (see FIG. 5C), trench networks intersecting at right angles (see FIG. 5D), as well as other angles (see FIG. 5E), as well as other regular and irregular trench configurations.

The drug containing depressions can be of any size that provides the features of the invention. Commonly, the medical devices of the invention contain drug-containing depressions whose smallest lateral dimension (e.g., the diameter for a cylindrical depression, the width for an elongated depression such a trench, etc.) is less than 10 mm (10000 µm), for example, ranging from 10,000 µm to 5000 µm to 2500 µm to 1000 µm to 500 µm to 250 µm to 100 µm to 50 µm to 10 µm to 5 µm to 2.5 µm to 1 µm or less.

Figure 6A:
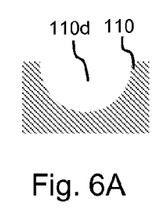
FIGS. 6A-6E are schematic cross-sectional views illustrating various depression configurations, which may be employed in various embodiments of the invention.
Figure 6B:
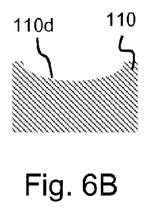
Figure 6C:
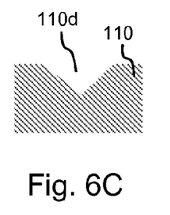
Figure 6D:
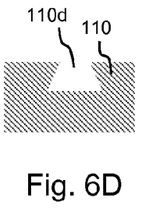
Figure 6E:
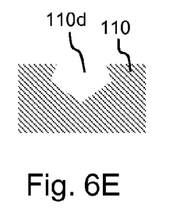

As indicated above, in some embodiments, the depressions 110*d* extend only partially into the substrate 110, for example, being in the form of blind holes, trenches, etc. Such depressions 110*d* may have a variety of cross-sections, such as semicircular cross-sections (see, e.g., FIG. 6A), semi-oval cross-sections (see, e.g., FIG. 6B), polygonal cross-sections, including triangular (see, e.g., FIG. 6C), quadrilateral (see, e.g., FIG. 6D) and penta-lateral (see, e.g., FIG. 6E) cross-sections, as well as other regular and irregular cross-sections. In certain embodiments, the depressions are high aspect ratio depressions, meaning that the depth of the depression is greater than the width of the depression, for example, ranging from 1.5 to 2 to 2.5 to 5 to 10 to 25 or more times the width. In certain other embodiments, the depressions are low aspect ratio depressions, meaning that the depth of the depression is less than the width of the depression, for example, ranging from 0.75 to 0.5 to 0.4 to 0.2 to 0.1 to 0.04 or less times the width.

Examples of techniques for forming depressions in substrates (e.g., holes, trenches, etc.), include molding techniques, direct removal techniques, and mask-based removal techniques. In molding techniques, a mold may be provided with various protrusions, which after casting the substrate of interest, create depressions in the substrate. Various direct and mask-based removal techniques are discussed below.

As previously indicated, in the present invention, the depressions further contain (i.e., they are at least partially filled with) one or more therapeutic agents (i.e., they may be used singly or in combination). The therapeutic agents may be present in pure form or admixed with another material, for example, a diluent, filler, excipient, matrix material, etc. Materials for these purposes may be selected, for example, from suitable members of the polymers listed below, among many other possible materials (e.g., small molecule chemical species). Where therapeutic agents are used in combination, one therapeutic agent may provide a matrix for another therapeutic agent.

By varying the size (i.e., volume) and number of the depressions, as well as the concentration of the therapeutic agents within the depressions, a range of therapeutic agent loading levels can be achieved. The amount of loading may be determined by those of ordinary skill in the art and may ultimately depend, for example, upon the disease or condition being treated, the age, sex and health of the subject, the nature (e.g., potency) of the therapeutic agent, or other factors.

As previously indicated, in the medical devices of the present invention, transport of chemical species from the therapeutic-agent-containing depressions, into these depressions, or both, is regulated by the porous membrane(s) disposed over the depressions. The pores of these transport-controlling regions are generally substantially smaller than the smallest lateral dimensions of the therapeutic-agent-containing depressions over which they are positioned (e.g., smaller than the width of a hole or trench, etc.). The pores of the release-controlling regions may be parallel to one another, they may be interconnected or both. They may be regular (e.g., cylindrical, etc.) or irregular in geometry.

As used herein, a "porous" material is one that contains pores. Porous membranes having a wide variety of pore sizes may be employed in the present invention. Pore sizes may range, for example, from nanopores (i.e., pores having widths of 50 nm or less), which include micropores (i.e., pores having widths smaller than 2 nm) and mesopores (i.e., pores having a widths ranging from 2 to 50 nm), to macropores (i.e., pores having widths that are larger than 50 nm). As used herein, a nanoporous surface is one that comprises nanopores (commonly at least $10^6$, $10^9$, $10^{12}$ or more nanopores per $cm^2$), a microporous surface is one that comprises micropores, a mesoporous surface is one that comprises mesopores, and a macroporous surface is one that comprises macropores.

Nanoporous materials have the potential to revolutionize drug delivery. For example, iMEDD, Inc. has created silicon membranes with parallel channels ranging from 4 to 50 nm. Diffusion rates of various solutes through such membranes have been measured and conform to zero-order kinetics in some instances (i.e., release is constant with time). This is in contrast with typical situations in which drug diffusion rates decay with time, because the concentration gradient, and thus the driving force for diffusion, is also decaying with time. One explanation for zero order behavior is that, by making the diameter of the nanopores only slightly larger than that of the drug, the nanopores act as bottlenecks, forcing the drugs to proceed in a substantially single-file fashion through the membrane. iMedd claims that the membranes can be engineered to control rates of diffusion by adjusting channel width in relation to the size of solutes. When the proper balance is struck, zero-order diffusion kinetics is possible. iMedd has produced a drug delivery device which consists of a drug-filled enclosure which is fitted with a nanoporous membrane as the only connection between the internal reservoir of the device and the external medium. See, e.g., Rita D'Aquino, "Good Drug Therapy: It's Not Just the Molecule—It's the Delivery" www.cepmagazin.org. February 2004 CEP, pp. 15S-17S; T. Desai et al., "Use of Microfabricated 'Nanopore' Membranes as a Rate-Limiting Barrier to Diffusion of Small and Large Molecules: Possible Role in Drug Delivery," *BioMems and Nanotechnology World* 2001; and Pub No. US 2003/0064095 to Martin et al.

Thus, depending on the pore size, it is known that nanoporous regions having parallel or near parallel pore structures can release chemical species such as therapeutic agents in accordance with zero order kinetics. In other less-structured release-controlling regions, the chemical species may travel through the region via interconnected networks of pores. In some instances, the lateral dimensions (e.g., the radii) of the interconnected pores approach the lateral dimensions (e.g., the hydrated radius) of the chemical species that is being transported. Consequently, the chemical species may move within, and ultimately be released from, pores of these diameters (as opposed to being trapped by pores having smaller radii). Under such circumstances, the interactions between the chemical species and the walls of the nanopores will have a significant effect upon the transport that is observed. Indeed, as the diameter of the pore approaches the diameter of the chemical species that is being transported, the surface interactions begin to dominate transport. See, e.g., Tejal A. Desai, Derek Hansford and Mauro Ferrari, "Characterization of micromachined silicon membranes for immunoisolation and bioseparation applications" J. Membrane Science, 159 (1999) 221-231, which describes insulin release through silicone nanomembranes.

Pores may also promote cell adhesion and/or proliferation. Enhanced cell adhesion to and proliferation upon textured structures, including porous structures, is a well-known phenomenon. For example, feature sizes less than 100 nm are believed to allow adhesion of proteins such as fibronectin, laminin, and/or vitronectin to the surface of the nanofiber-textured layer, and to provide a conformation for these proteins that better exposes amino acid sequences such as RGD and YGSIR which enhance endothelial cell binding. See, e.g., *Standard handbook of biomedical engineering and design*, Myer Kutz, Ed., 2003 ISBN 0-07-135637-1, p. 16.13. Moreover, nanotexturing increases surface energy, which is believed to increase cell adhesion. See, e.g., J. Y. Lim et al., *J. Biomed. Mater. Res.* (2004) 68A(3): 504-512. In this regard, submicron topography, including pores, fibers, and elevations in the sub-100 nm range, has been observed for the basement membrane of the aortic valve endothelium as well as for other basement membrane materials. See R. G. Flemming et al., *Biomaterials* 20 (1999) 573-588, S. Brody et al., *Tissue Eng.* 2006 February; 12(2): 413-421, and S. L. Goodman et al., *Biomaterials* 1996; 17: 2087-95. Goodman et al. employed polymer casting to replicate the topographical features of the subendothelial extracellular matrix surface of denuded and distended blood vessels, and they found that endothelial cells grown on such materials spread faster and appeared more like cells in their native arteries than did cells grown on untextured surfaces. Formation of a functional endothelial cell layer is an effective way to reduce or eliminate inflammation and thrombosis, which are sometimes associated with implantable devices. See, e.g., J. M. Caves et al., *J. Vasc. Surg.* (2006) 44: 1363-8.

As previously indicated, components for use in the medical devices of the present invention (e.g., substrates, porous membranes, etc.) may be selected from a variety of materials including (a) biostable and biodegradable organic materials such as polymeric materials, and (b) inorganic materials such as biostable and biodegradable metallic materials (e.g., metals and metal alloys) and biostable and biodegradable non-metallic inorganic materials (e.g., carbon, semiconductors, glasses, ceramics, etc.) As also noted above, the TEC of the material is taken into account in the material selection process, particularly where selecting the materials for the substrates and porous membranes.

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals (e.g., metals such as gold, niobium, platinum, palladium, iridium, osmium, rhodium, titanium, tantalum, tungsten, ruthenium, iron, zinc and magnesium), metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodegradable alloys of magnesium, zinc and/or iron.

Specific examples of organic materials include polymers (biostable or biodegradable) and other high molecular weight organic materials, and may be selected, for example, from suitable materials containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

Several specific examples of component materials (among many other possibilities) are listed below, along with their approximate TEC values. For more examples, see, e.g., *ASM Ready Reference: Thermal properties of Metals*, ASM International, Materials Park, Ohio, USA; W. D. Callister, *Materials Science and Engineering: An Introduction*, 7th Edition, 2006, page W5; M. A. Occhionero et al., "Aluminum Silicon Carbide (AlSiC) Microprocessor Lids and Heat Sinks for Integrated Thermal Management Solutions", 2000 HDI Conf., Denver, Colo., Apr. 26-28, 2000, pp. 1-5; and "Chart of COE's Coefficient of Thermal Expansion" at http://lucasmilhaupt.com.

Relatively high TEC metallic inorganic components include zinc and its alloys (19-35 ppm/° C.), magnesium alloys (26-29 ppm/° C.), Cr—Ni—Fe superalloys (17-19 ppm/° C.), stainless steel (11-19 ppm/° C.) including austenitic stainless steels (16-18 ppm/° C.), cast nodular or ductile irons and wrought irons (12-19 ppm/° C.), nickel based superalloys (14-18 ppm/° C.), cobalt based superalloys (12-17 ppm/° C.), nickel and its alloys (12-17 ppm/° C.), Cr—Ni—Co—Fe superalloys (14-16 ppm/° C.) and gold (14 ppm/° C.), among many others.

Relatively low TEC metallic inorganic components include tungsten (4 ppm/° C.), molybdenum and its alloys (6 ppm/° C.), hafnium (6 ppm/° C.), zirconium and its alloys (6 ppm/° C.), osmium and tantalum (6 ppm/° C.) and iridium (7 ppm/° C.), among many others.

Examples of non-metallic inorganic components include silicon (3 ppm/° C.), boron carbide (3 ppm/° C.), silicon carbide 4 ppm/° C.), zirconia (6 ppm/° C.), and alumina (7 ppm/° C.), among many others. The preceding are low TEC materials (relative to the above relatively high TEC metallic inorganic components).

Examples of organic components include polymers such as polyethylene (110-200 ppm/° C.), polypropylene (150-180 ppm/° C.), polystyrene (90-150 ppm/° C.), polytetrafluoroethylene (130-220 ppm/° C.), and nylon 6,6 (140 ppm/° C.), among many others, which tend to have TEC values that are significantly higher than the above inorganic components.

Direct removal techniques as well as mask-based removal techniques, in which masking is used to protect material that is not to be removed, may be used in accordance with the invention to create voids in substrates (e.g., holes, trenches, etc.), to form pores for porous membranes, or to sculpt stent struts from tubes, among other processes.

Direct removal techniques include those in which material is removed through contact with solid tools (e.g., microdrilling, micromachining, etc., using high precision equipment such as high precision milling machines and lathes) and those that remove material without the need for solid tools (e.g., those based on directed energetic beams such as laser, electron, and ion beams). In the latter cases, techniques based on diffractive optical elements (DOEs), holographic diffraction, and/or polarization trepanning, among other beam manipulation methods, may be employed to generate patterns as desired. Using these and other techniques, multiple voids can be formed in a material layer at once.

Mask-based techniques include those in which the masking material contacts the material to be machined (e.g., where masks are formed using known lithographic techniques, including optical, ultraviolet, deep ultraviolet, electron beam, and x-ray lithography) and techniques in which the masking material does not contact the material to be machined, but which is provided between a directed source of excavating energy and the material to be machined (e.g., opaque masks having apertures formed therein, as well as semi-transparent masks such as gray-scale masks which provide variable beam intensity and thus variable machining rates). One process, known as columnated plasma lithography, is capable of producing X-rays for lithography having wavelengths on the order of 10 nm. Material is removed in regions not protected by the above masks using any of a range of processes including physical processes (e.g., thermal sublimation and/or vaporization of the material that is removed), chemical processes (e.g., chemical breakdown and/or reaction of the material that is removed), or a combination of both. Specific examples of removal processes include wet and dry (plasma) etching techniques, and ablation techniques based on directed energetic beams such as electron, ion and laser beams. A lithography-based process for forming nanoporous silicon is described, for example, in L. Leoni et al. "Nanoporous Platforms for Cellular Sensing and Delivery," *Sensors* 2002, 2, 111-120.

In those embodiments of the invention where laser light is used for material removal (e.g., for formation of depressions, pores, stent struts, etc.), shorter wavelength light may be preferred. There are several reasons for this. For example, shorter wavelength light such as UV and deep-UV light can be imaged to a smaller spot size than light of longer wavelengths (e.g., because the minimum feature size is limited by diffraction, which increases with wavelength). Such shorter wavelength light is also typically relatively photolytic, displaying less thermal influence on surrounding material. Moreover, many materials have high absorption coefficients in the ultraviolet region. This means that the penetration depth is small, with each pulse removing only a thin layer of material, thereby allowing precise control of the drilling depth. Various lasers are available for laser ablation, including excimer lasers, solid state lasers such as those based on Nd:YAG and Nd:vanadate, among other crystals, metal vapor lasers, such as copper vapor lasers, and femtosecond lasers. Further information on lasers and laser ablation may be found in T. Lippert et al., "Chemical and spectroscopic aspects of polymer ablation: Special features and novel directions," *Chem. Rev.*, 103(2): 453-485 February 2003; J. Meijer et al., "Laser Machining by short and ultrashort pulses, state of the art and new opportunities in the age of photons," *Annals of the CIRP*, 51(2), 531-550, 2002, and U.S. Pat. No. 6,517,888 to Weber.

It is noted that there is a great amount of available know-how in the semiconductor industry for etching holes (e.g., vias), trenches and other voids in various materials. For this reason, in some embodiments of the invention, material may be removed from materials for which processing is routine in the semiconducting industry including semiconducting materials such as silicon, conductive materials such as metals and metal alloys, and insulating materials such as silicon oxide, silicon nitride and various metal oxides.

For the formation of porous membranes, in some embodiments, a precursor region is formed which comprises first and second materials. Subsequently, the precursor region is subjected to conditions where the first material is either reduced in volume or eliminated from the precursor region. By providing nanoscale domains of the first material within the precursor region, a nanoporous region may be formed. Materials for forming such removable or size-reducible nanoscale domains include (a) materials that are converted into gaseous species upon heating, for example, materials that sublime, materials that melt and then evaporate, and materials that form gaseous reaction products such as combustible materials, (b) metal oxides which may be reduced to their corresponding metal, resulting in a loss in volume, (c) materials which are dissolved or otherwise removed in a solution, and so forth.

Some of these techniques rely on the ability of certain materials to phase separate into nanoscale domains. For example, nanoporous regions may be produced from a metal alloy that contains two or more metals of differing nobility and at least one of the less-noble metals is oxidized and removed from the alloy, thereby forming a nanoporous region. In these embodiments, the at least one less-noble metal corresponds to the nanoscale domains described above. Various methods are available for oxidizing and removing the less noble metal(s) from the metal mixture, including (i) contact with an appropriate acid (e.g., nitric acid), (ii) application of a voltage of sufficient magnitude and bias during immersion in a suitable electrolyte, and (iii) heating in the presence of oxygen, followed by dissolution of the resultant oxide. Examples include alloys of essentially any substantially non-oxidizing noble metal (e.g., gold, platinum, etc.) having nanoscale domains of essentially any metal that can be removed (e.g. Zn, Fe, Cu, Ag, etc.). Specific examples of suitable alloys include alloys comprising gold and silver (in which the silver is oxidized and removed), alloys comprising gold and copper (in which the copper is oxidized and removed), and so forth. Further details concerning de-alloying can be found, for example, in J. Erlebacher et al., "Evolution of nanoporosity in de-alloying," Nature, Vo. 410, 22 Mar. 2001, 450-453; A. J. Forty, "Corrosion micromorphology of noble metal alloys and depletion gilding," Nature, Vol. 282, 6 Dec. 1979, 597-598; R. C. Newman et al., "Alloy Corrosion," MRS Bulletin, July 1999, 24-28; and Pub. No. US 2004/0148015 assigned to Setagon. Porous membranes for use in the present invention may be formed by dealloying an alloy having the shape desired for the porous membrane (e.g., sheet, tube, etc.) as described in these references.

High-density arrays of nanopores may also be formed based on the self-assembly of nanoscale domains using block copolymers. Cylindrical nanopores may be formed, for example, using diblock copolymers composed of polymethylmethacrylate (PMMA) and polystyrene (PS). The molecular weight and volume fraction of styrene may be selected such that the copolymer self-assembles into arrays of PMMA cylinders hexagonally packed in a PS matrix. The PMMA cylinders may be oriented parallel to each other by applying an electric field, while the copolymer film is heated above the glass transition temperature. Deep ultraviolet exposure may be used to degrade the PMMA domains and simultaneously crosslink the PS matrix. The PMMA domains may be selectively removed by rinsing the film with acetic acid, yielding a PS film with ordered nanopores. For further information, see, e.g., H. X. He and N. J. Tao, "Electrochemical fabrication of metal nanowires" in Encyclopedia of Nanoscience and Nanotechnology, Eds., N. S. Nalwa, American Scientific Publishers, 2003, and the references cited therein. Porous membranes for use in the present invention may be formed using such techniques. The shape of the electrical field that is applied will clearly depend upon the geometry of the porous membrane that is being formed (e.g., planar, tubular, etc.).

Porous membranes may also be formed using deposition techniques wherein layers are formed on a sacrificial substrate, which is later removed (e.g., by dissolution, etc.). The geometry of the substrate will dictate the geometry of the porous membrane that is ultimately formed (e.g., planar, tubular, etc.)

For example, in some embodiments, nanoporous regions may be formed using physical vapor deposition (PVD) techniques. For example, two or more materials may be deposited by PVD, followed by removal of one or more of the materials to produce a nanoporous region. For instance, two or more metals may be simultaneously deposited via PVD (e.g., by sputtering separate targets of a single metal or by sputtering a single target containing multiple metals), followed by annealing if necessary to cause phase separation, which is followed by de-alloying, for example, using techniques such as those described above.

Chemical vapor deposition (CVD) techniques, including low-pressure chemical vapor deposition (LPCVD) processes and plasma-enhanced chemical vapor deposition (PECVD) processes, may be used in the formation of nanoporous regions. For example, it is known to deposit nanoporous silicon dielectric films (e.g., silicon oxide films such as silicon dioxide) by PECVD using organosilicate precursor compounds such as tetraethylorthosilicate (TEOS), typically in the presence of an oxidant such as $N_2O$, $O_2$, $O_3$, $H_2O_2$, etc. See e.g., United States Patent Application No. 2002/0142579 to Vincent et al. As another example, it is known to deposit nanoporous silicon oxycarbide films (specifically SiOCH, also known as hydrogenated silicon oxycarbide) by PECVD oxidation of $(CH_3)_3SiH$ in the presence of an oxidant (i.e., $N_2O$). See, e.g., D. Shamiryan et al., "Comparative study of SiOCH low-k films with varied porosity interacting with etching and cleaning plasma," J. Vac. Sci. Technol. B, 20(5), September/October 2002, pp. 1923-1928.

As another example, in hot-filament CVD (HFCVD), also known as pyrolytic or hot-wire CVD, a precursor gas is thermally decomposed by a resistively heated filament. The resulting pyrolysis products then adsorb onto a substrate maintained at a lower temperature (typically around room temperature) and react to form a film. For example, a fluorocarbon polymer film may be prepared by exposing a fluorocarbon monomer (e.g., hexafluoropropylene oxide, among others) to a source of heat having a temperature sufficient to pyrolyze the monomer and produce a reactive species that promotes polymerization. By maintaining the substrate region in the vicinity of the reactive species and maintaining the substrate region at a substantially lower temperature than that of the heat source, deposition and polymerization of the reactive species on the structure surface are induced. In other embodiments, fluorocarbon-organosilicon copolymer films are prepared by exposing a fluorocarbon monomer (e.g., hexafluoropropylene oxide, among others) and an organosilicon monomer (e.g., hexamethylcyclotrisiloxane or octamethylcyclotetrasiloxane, among others) to the heat source. Due to the nucleation and growth mechanisms in the HFCVD processes, nanoporous films can be made using HFCVD. For further information, see, e.g., United States Patent Application No. 2003/0138645 to Gleason et al., U.S. Pat. No. 6,156,435 to Gleason et al., and K. K. S. Lau et al., "Hot-wire chemical vapor deposition (HWCVD) of fluorocarbon and organosilicon thin films," Thin Solid Films, 395 (2001) pp. 288-291.

In some embodiments, porous regions are formed using electrochemical methods. For example, materials with nanoscale domains may be formed by first incorporating suspended nanoparticles into a matrix that is formed by electrodeposition and/or electroless deposition. (For example, nanoparticles that are dispersed by adsorbing cations on their surfaces, are known to travel to the cathode where electrodeposition takes place, such that the nanoparticles are incorporated into the deposited layer.) Once formed, such nanoscale domains are subsequently reduced in size as discussed above (e.g., by sublimation, evaporation, combustion, dissolution, etc.).

Another example of an electrochemical technique is the anodization of aluminum to form porous alumina. The individual pores that are formed in the alumina upon anodization may be ordered into a hexagonally packed structure, with the diameter of each pore and the separation between two adjacent pores being controlled by changing the anodization conditions. Pore ordering has been shown to be improved using high-purity aluminum films, which are preannealed and electropolished Pore ordering also depends on anodization conditions, such as anodization voltage and the electrolyte. Pore ordering may be promoted through the use of a pre-texturing process in which an array of shallow concave features is initially formed on aluminum by indentation. Pore ordering may also be promoted by employing a two-step anodization method. The first step involves anodization of high purity aluminum to form a porous alumina layer. This layer is then dissolved, yielding a patterned aluminum substrate with an ordered array of concave features formed during the first anodization step. The ordered concave features then serve as the initial sites to form a highly ordered pore array in a second anodization step. Aluminum anodization normally results in a porous alumina structure which is separated from the aluminum substrate by a layer of $Al_2O_3$. The $Al_2O_3$ layer and aluminum substrate may then be removed to form a free-standing porous alumina membrane. For further information on anodization, see, e.g., H. X. He and N. J. Tao, "Electrochemical fabrication of metal nanowires" in Encyclopedia of Nanoscience and Nanotechnology, Eds., N. S. Nalwa, American Scientific Publishers, 2003, and the references cited therein. See also E. E. L. Swan, K. C. Popat, C. A. Grimes, T. A. Desai, "Fabrication and evaluation of nanoporous alumina membranes for osteoblast culture," Journal of Biomedical Materials Research Part A, Volume 72A, Issue 3, Pages 288-295, Published Online: 14 Jan. 2005, which describes osteoblast response to surface topography in anodized nanoporous alumina membranes. Alumina membranes with pore sizes ranging from 30 to 80 nm are reported.

Porous membranes for use in the present invention may be formed from high purity aluminum in the desired shape of the porous membrane (e.g., sheet, tube, etc.), by subjecting it to treatment as described in these references. As will be understood by those of ordinary skill in the art, the geometry of the electrochemical apparatus employed (e.g., the shape and placement of the counter-electrode, etc.) will vary depending on the geometry of the material being anodized. For example, a flat counter-electrode may be used to process planar aluminum materials, a rod-shaped or hollow cylindrical counter-electrode may be used to process tubular aluminum materials, and so forth.

In some embodiments of the invention, nanoporous regions are formed on a suitable substrate using sol-gel techniques, and the substrate is subsequently removed. The starting materials that are used in the preparation of sol-gel regions are frequently inorganic metal salts, metallic complexes (e.g., metal acetylacetonate complexes), or organometallic compounds (e.g., metal alkoxides). Typically, the starting material is subjected to hydrolysis and polymerization (sometimes referred to as a condensation) reactions to form a colloidal suspension, or "sol". Further processing of the sol enables ceramic materials to be made in a variety of different forms. For instance, thin films can be produced on a substrate, for example, by spray coating, coating with an applicator (e.g., by roller or brush), spin-coating, or dip-coating of the sol onto the substrate, whereby a wet gel is formed. Where dip coating is employed, the rate of withdrawal from the sol can be varied to influence the properties of the film. The wet gel is then dried. The porosity of the gel can be regulated in a number of ways, including, for example, varying the solvent/water content, varying the aging time, varying the drying method and rate, and so forth. In certain embodiments, sol-gel processing is carried out at low temperatures (e.g., temperatures of 15-35° C.). In other embodiments, the sol-gel is subjected to high temperatures, for example, temperatures of 100° C., 200° C., 300° C., 400° C., 500° C., or more. Such high temperatures commonly reduce the porosity of the sol-gel, while at the same time increasing its mechanical strength. Further information concerning sol-gel materials can be found, for example, in Viitala R. et al., "Surface properties of in vitro bioactive and non-bioactive sol-gel derived materials," Biomaterials. 2002 August; 23 (15):3073-86; Radin, S. et al., "In vitro bioactivity and degradation behavior of silica xerogels intended as controlled release materials," Biomaterials. 2002 August; 23 (15):3113-22; Nicoll S. B., et al., "In vitro release kinetics of biologically active transforming growth factor-beta 1 from a novel porous glass carrier," Biomaterials. 1997 June; 18 (12):853-9; Santos, E. M. et al., "Sol-gel derived carrier for the controlled release of proteins," Biomaterials. 1999 September; 20 (18):1695-700; Radin, S. et al., "Silica sol-gel for the controlled release of antibiotics. I. Synthesis, characterization, and in vitro release," J Biomed Mater Res. 2001 November; 57 (2):313-20; Aughenbaugh, W. et al., "Silica sol-gel for the controlled release of antibiotics. II. The effect of synthesis parameters on the in vitro release kinetics of vancomycin," J Biomed Mater Res. 2001 Dec. 5; 57 (3):321-6; Santos, E. M. et al., "Si—Ca—P xerogels and bone morphogenetic protein act synergistically on rat stromal marrow cell differentiation in vitro," J Biomed Mater Res. 1998 July; 41 (1):87-94.

High porosity, uniform-pore-size mesoporous silicon oxide and aluminum oxide films may also be prepared by sol-gel methods using block copolymers as the structure-directing agents. For example, J.-A. Paik et al. "Micromachining of mesoporous oxide films for microelectromechanical system structures," J. Mater. Res., Vol. 17, No. 8, August 2002, 2121 has reported the formation of films that are over 50% porous with uniform pores of 8-nm average diameter.

For further techniques suitable for forming porous membranes, see, e.g., Pub. No. US 2006/0129215, Pub. No. US 2006/0127443, and U.S. Ser. No. 11/388,604 entitled "Medical Devices having Nanoporous Coatings for Controlled Therapeutic Agent Delivery" and the references cited therein.

A tubular porous membrane may also be formed from a porous rectangular sheet (assuming that it is sufficiently flexible) by rolling the sheet into the shape of a tube and affixing the edges to one another (e.g., by forming a butt-joint or an overlapping joint).

"Biologically active agents," "drugs," "therapeutic agents," "pharmaceutically active agents," "pharmaceutically active materials," and other related terms may be used interchangeably herein and include genetic therapeutic agents, non-genetic therapeutic agents and cells. A wide variety of therapeutic agents can be employed in conjunction with the present invention. Numerous therapeutic agents are described here.

Suitable non-genetic therapeutic agents for use in connection with the present invention may be selected, for example, from one or more of the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists such as rosiglitazone, pioglitazone, netoglitazone, fenofibrate, bexaotene, metaglidasen, rivoglitazone and tesaglitazar, (bb) prostaglandin E agonists such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, and (ff) phospholipids including phosphorylcholine, phosphatidylinositol and phosphatidylcholine.

Preferred non-genetic therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Suitable genetic therapeutic agents for use in connection with the present invention include anti-sense DNA and RNA as well as DNA coding for the various proteins (as well as the proteins themselves) and may be selected, for example, from one or more of the following: (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., PCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Further therapeutic agents, not necessarily exclusive of those listed above, have been identified as candidates for vascular treatment regimens, for example, as agents targeting restenosis (anti-restenotic agents). Suitable agents may be selected, for example, from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD (orgotein), SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Numerous additional therapeutic for the practice of the present invention may be selected from suitable therapeutic agents disclosed in U.S. Pat. No. 5,733,925 to Kunz.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising as components:
   (a) a substrate component comprising a depression that is at least partially filled with a therapeutic-agent-containing material that comprises a first therapeutic agent, and
   (b) a porous membrane component engaged with the substrate component and disposed over the depression such that it regulates transport of chemical species between the depression and the exterior of the device upon implantation or insertion of the device into a subject, wherein one component having an inner surface at least partially surrounds the other component having an outer surface, wherein the inner surface is engaged with the outer surface, wherein the components are formed from materials that have a different thermal expansion coefficient (TEC), wherein either (i) wherein both components expand upon heating such that the inner surface moves outwardly relative to the outer surface and such that the porous membrane component disengages from the substrate component upon heating the medical device and wherein the component that at least partially surrounds the other component is the component with the higher TEC or (ii) wherein both components contract upon cooling such that the inner surface moves outwardly relative to the outer surface and such that the porous membrane component disengages from the substrate component upon cooling the medical device and wherein the component that at least partially surrounds the other component is the component with the lower TEC, and wherein the porous membrane component is engaged with the substrate component upon implantation or insertion of the device into a subject.

2. The implantable or insertable medical device of claim 1, wherein the TEC of one component is at least 10% higher than the TEC of the other component.

3. The implantable or insertable medical device of claim 1, wherein both components comprise an annular cross-section.

4. The implantable or insertable medical device of claim 1, wherein the substrate component comprises an annular cross-section and the porous membrane component comprises a circular cross-section.

5. The implantable or insertable medical device of claim 1, wherein the substrate component comprises a circular cross-section and the porous membrane component comprises an annular cross-section.

6. The implantable or insertable medical device of claim 1, wherein the porous membrane component at least partially surrounds the substrate component.

7. The implantable or insertable medical device of claim 1, wherein the substrate component at least partially surrounds the porous membrane component.

8. The implantable or insertable medical device of claim 1, wherein the porous membrane component disengages from the substrate component upon heating the medical device and wherein the component that at least partially surrounds the other component is the component with the higher TEC.

9. The implantable or insertable medical device of claim 1, wherein the porous membrane component disengages from the substrate component upon cooling the medical device and wherein the component that at least partially surrounds the other component is the component with the lower TEC.

10. The implantable or insertable medical device of claim 1, wherein said substrate component comprises a plurality of depressions.

11. The implantable or insertable medical device of claim 1, wherein said depression is a blind hole or a trench.

12. The implantable or insertable medical device of claim 1, wherein said porous membrane component is a nanoporous membrane component.

13. The implantable or insertable medical device of claim 1, wherein said medical device is adapted for implantation or insertion into the coronary vasculature, peripheral vascular system, esophagus, trachea, colon, biliary tract, urogenital system, or brain.

14. The implantable or insertable medical device of claim 1, wherein said medical device is selected from a drug delivery device, an implant, a stent, a graft, a filter, a catheter, a defibrillator, a chronic rhythm management lead and a neuromodulation device.

15. The implantable or insertable medical device of claim 1, wherein the therapeutic-agent-containing material further comprises a material in addition to said first therapeutic agent.

16. The implantable or insertable medical device of claim 1, wherein the therapeutic-agent-containing material further comprises a second therapeutic agent.

17. The implantable or insertable medical device of claim 1, wherein said therapeutic agent is released from said device and wherein the porous membrane component regulates transport of said therapeutic agent.

18. The implantable or insertable medical device of claim 17, wherein the release is substantially zero-order.

19. The implantable or insertable medical device of claim 1, wherein said therapeutic agent is selected from one or more of the group consisting of anti-thrombotic agents, anti-proliferative agents, anti-inflammatory agents, anti-restenotic agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, TGF-$\beta$ elevating agents, and agents that interfere with endogenous vasoactive mechanisms.

20. The implantable or insertable medical device of claim 1, wherein the medical device is a stent, wherein the substrate component is a metallic substrate component that comprises depressions on its abluminal surface that are at least partially filled with a therapeutic-agent-containing material that comprises an antirestenotic agent, and wherein the porous membrane component is a metallic membrane component that at least partially surrounds the substrate component.

* * * * *